United States Patent [19]
Guadagno et al.

[11] Patent Number: 5,085,758
[45] Date of Patent: Feb. 4, 1992

[54] CONTAINER FOR ELECTROPHORETIC GEL

[75] Inventors: Philip A. Guadagno, Vidor; Terry L. McNeely, Beaumont, both of Tex.

[73] Assignee: Helena Laboratories Corporation, Beaumont, Tex.

[21] Appl. No.: 698,383

[22] Filed: May 10, 1991

Related U.S. Application Data

[62] Division of Ser. No. 527,354, May 23, 1990, Pat. No. 5,045,173.

[51] Int. Cl.$^5$ .................... B65D 85/48; B01D 61/42
[52] U.S. Cl. .................... 204/299 R; 204/182.8; 206/449; 206/451; 206/454; 206/456; 220/4.21
[58] Field of Search .............. 204/182.8, 299 R; 206/449, 451, 454, 456; 220/4 B, 4 E

[56] References Cited

U.S. PATENT DOCUMENTS

| | | | |
|---|---|---|---|
| 4,314,897 | 2/1982 | Monte et al. | 204/299 R |
| 4,511,034 | 4/1985 | Pan | 206/310 |
| 4,576,330 | 3/1986 | Schepp | 229/44 R |
| 4,709,810 | 12/1987 | Mayes | 206/205 |
| 4,741,814 | 5/1988 | Mayes et al. | 204/299 R |
| 4,759,838 | 7/1988 | Mayes et al. | 204/299 R |

*Primary Examiner*—John Niebling
*Assistant Examiner*—David G. Ryser
*Attorney, Agent, or Firm*—Spencer & Frank

[57] ABSTRACT

An electrophoretic gel container for protecting an electrophoresis plate during shipment and storage, the electrophoresis plate being the type including a substrate having a major surface and a gel layer adhered to a portion of the major surface with the substrate including a peripheral portion free of the gel layer. The container includes a top portion and a bottom portion which are sealingly engageable with one another. The top and bottom portions have cooperating projections such that the top and bottom may be interlocked together. The gel layer substrate includes alignment apertures and the container includes alignment sockets in the bottom portion and locking pins in the top portion. The alignment sockets extend through the alignment apertures in the electrophoresis plate and has locking pins engage the alignment sockets to further secure the electrophoresis plate against movement. The container top portion is provided with stacking posts to support and distribute weight when a plurality of containers are stacked vertically.

12 Claims, 4 Drawing Sheets

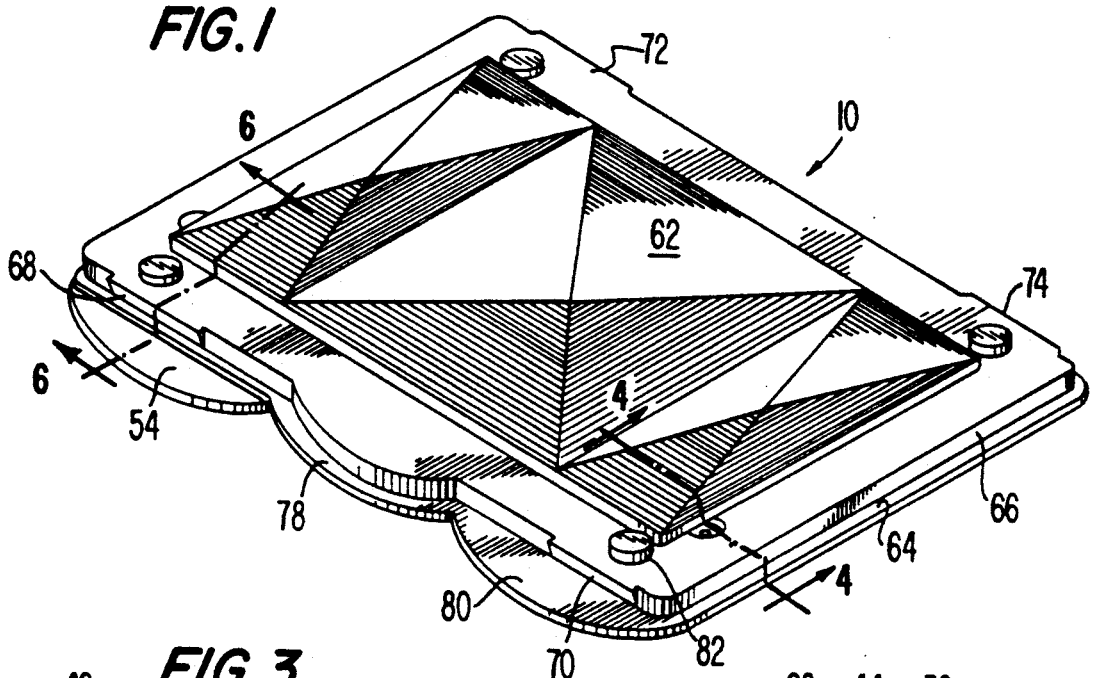
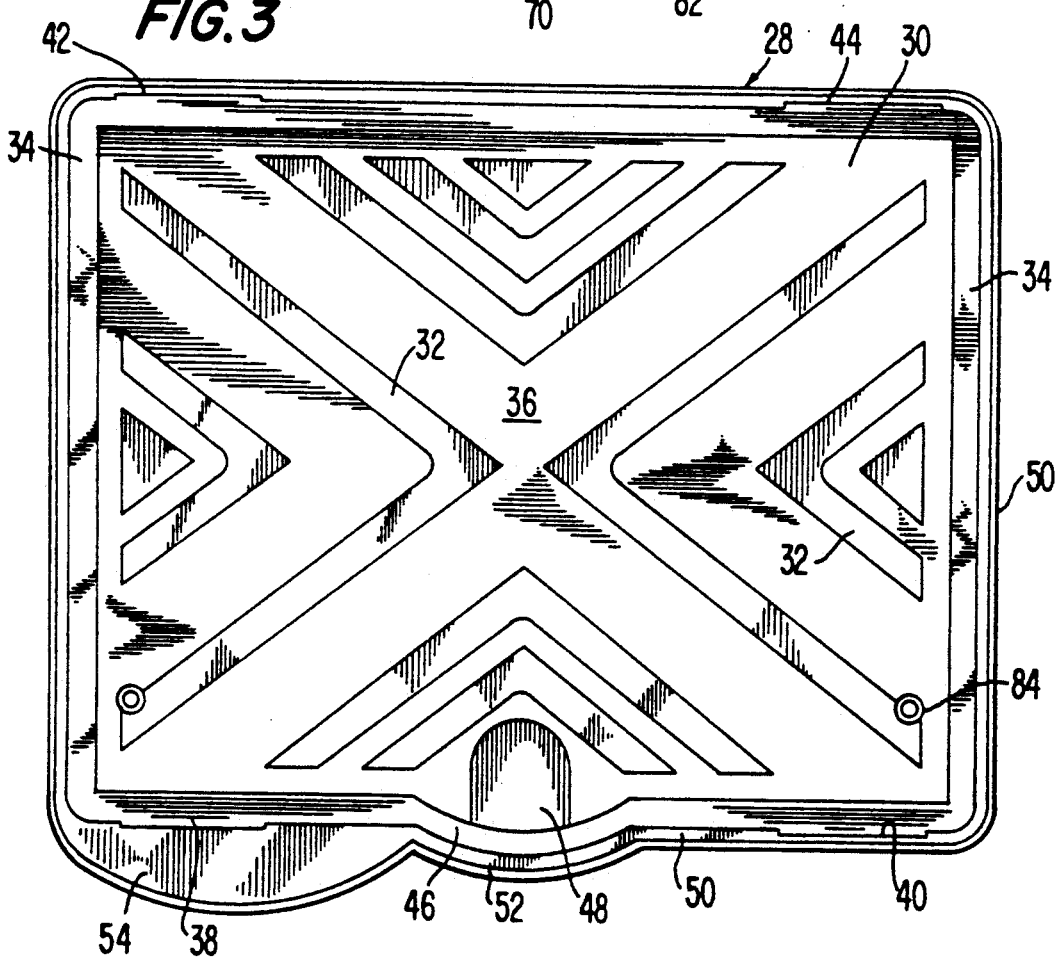

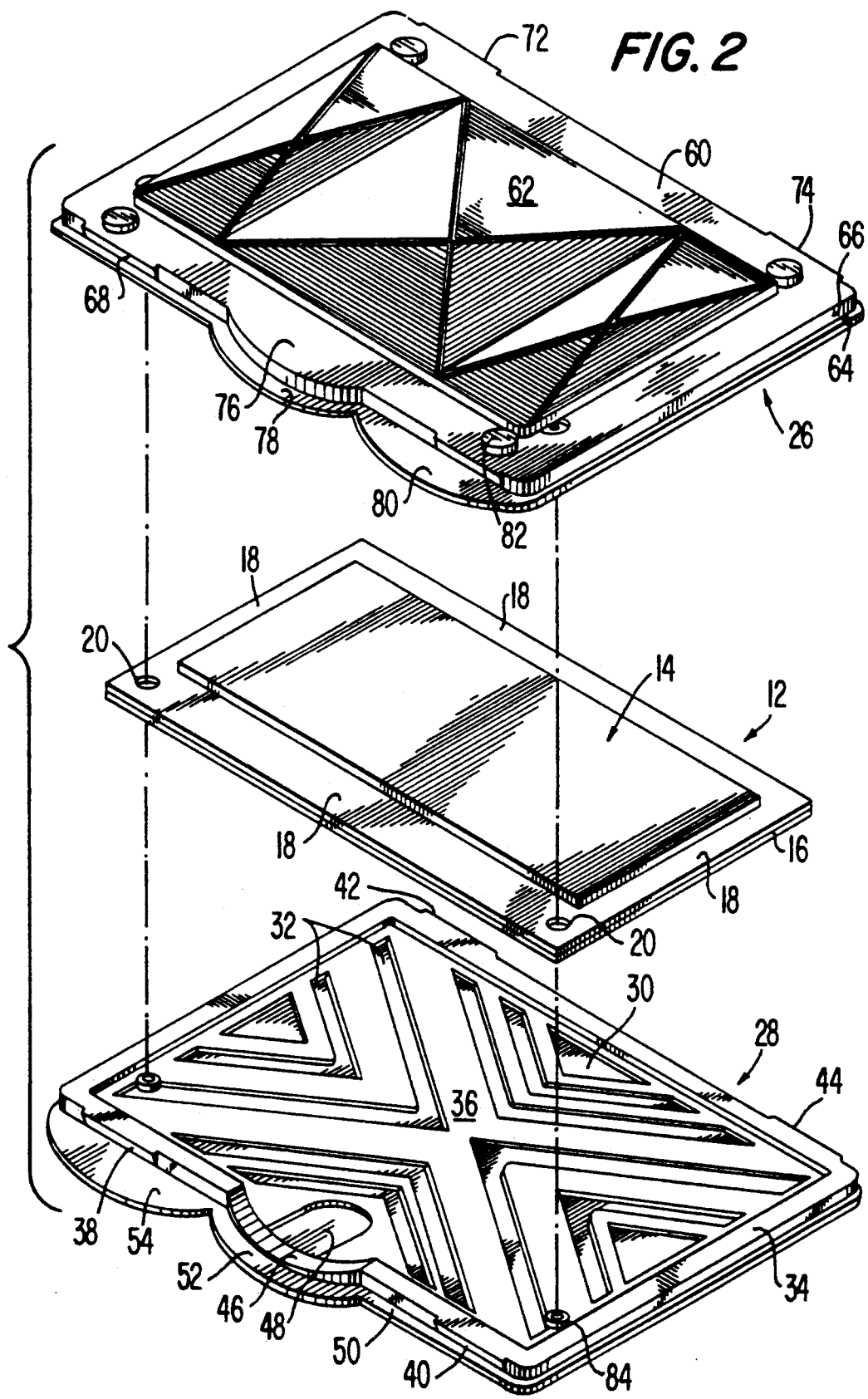

CONTAINER FOR ELECTROPHORETIC GEL

This is a division of application Ser. No. 07/527,354 filed May 23rd, 1990, now U.S. Pat. No. 5,045,173.

BACKGROUND OF THE INVENTION

1. Field of the Invention

The present invention relates generally to a procedure known as electrophoresis and, more particularly, the present invention is directed to a protective container for an electrophoretic media of the type referred to as an electrophoretic gel. The container supports the electrophoretic gel from the time of manufacture to the time of use. The container provides support for the gel as the electrophoretic gel is transported from one location to another, and when the electrophoretic gel is being stored.

2. Description of the Prior Art

Electrophoresis involves the placing of a sample substance, such as blood serum or urine, in a support medium. A direct current electrical potential is maintained across the support medium through the use of opposed electrodes. Support media characteristically include paper, agar, agarose, cellulose acetate and polyacrylamide. The electrical potential causes the colloidal particles in the sample substance to migrate toward one or the other electrodes. The amount of migration is determined by the electrical charges on the particles in the sample substance and the magnitude of the electrical potential. Particles with similar properties tend to migrate or group into defined areas and thus a determination may be made as to the amount of each class of substance present in sample.

It is important to the electrophoretic process that the support medium be uniform and free from imperfections. Agarose has been found to be an excellent support medium. The agarose is formed into a gel layer into which the sample substance is placed. An electrical potential is maintained across the gel layer and particle migration takes place. The gel layer may then be reacted with a chemical mixture or reagent to render the separation visible and readable by a trained technician. Different chemical mixtures may be employed to visualize different classes of separated substances.

When gel layers are to be used commercially, such as in clinical laboratories, the gel layers must be transported or shipped from the place of manufacture to the clinical laboratory and the gel layers must be stored until they are to be used. Heretofore, problem have occurred both in the shipping and in the storing of gel layers. The problems are twofold: physical damage to the gel layers and dehydration of the gel layers. Although the gel layers are usually adhered to a support substrate, and placed in containers, both damage to the gel layer and dehydration of the gel layer may still occur. The containers heretofore used normally take one of two forms: either separate top and bottom pieces which are to be secured together or top and bottom pieces which are hinged together and which are opened or closed. Containers are made of substantially rigid plastic such as styrene.

One approach to the protection of the gel layer is disclosed in U.S. Pat. No. 4,314,897 to Monte et al wherein the top and bottom portions of a container physically trap the upper and lower surfaces of the substrate onto which the gel layer is adhered. This precludes movement of the substrate thus tending to reduce damage to the gel. The sealing relationship between the container top and bottom also tends to reduce dehydration of the gel.

Another approach is illustrated in U.S. Pat. No. 4,709,810 to Mayes, assigned to the assignee of the present invention, wherein the substrate is maintained within closed, sealed container portions by water adhesion. The water adhesion tends to protect the gel layer from movement and the sealing of the container portions tends to reduce dehydration. Other prior art techniques include the provision of alignment apertures in the substrate and alignment pins in the container such that when the substrate (containing the gel layer) is placed within the container, the alignment pins of the container extend upwardly through the alignment apertures in the substrate to reduce lateral movement of the substrate. Alternate approaches are also illustrated in U.S. Pat. Nos. 4,741,814 and 4,759,838 both assigned to the assignee of the present invention.

Notwithstanding these prior art techniques, it has been found that the gel layer still tends to become damaged during shipment and storage primarily for two reasons. A first reason is that when a plurality of containers are shipped from one location to another, the containers are frequently rotated 90° onto one side or even rotated 180° and thus inverted, causing the substrate to move free of the alignment pins. Furthermore, when a plurality of containers are shipped or stored, the collective weight of the containers tends to damage some of the containers and the gel layer within one or more of the containers.

SUMMARY OF THE INVENTION

The present invention overcomes these shortcomings by providing an improved electrophoretic gel container which better protects the gel layer from damage during shipping and during storage.

The container of the present invention includes an improved means for retaining the substrate in a predetermined position, even if the container is inverted, to thus protect the gel layer. The container of the present invention includes improved reinforcement means to protect the containers from damage during shipment and storage. The container of the present invention further includes an improved interlock to assist in the prevention of dehydration and to provide increased structural rigidity of the closed container.

The container of the present invention may be formed as a one-piece, hinged unit or as two separate pieces. The container includes alignment pins for the gel layer substrate and when the container is closed, the alignment pins are partially deformed by projections in the container which projections remain within the alignment pins such that the substrate is maintained in a fixed position even if the container is inverted. Interfitting projections are provided such that when the container is closed the interfitting projections provide a force-fit seal thus reducing dehydration. The container of the present invention further includes reinforcement means for supporting the container and for distributing or transferring the force or weight which may be placed on the container thus preventing damage to the container and damage to the gel layer.

BRIEF DESCRIPTION OF THE DRAWINGS

The various objects, benefits and advantages of the present invention will become more apparent upon reading the following detailed description of the invention taken in conjunction with the drawings.

In the drawings, wherein like reference numerals identify corresponding components:

FIG. 1 is a perspective illustration of a container for an electrophoretic gel according to the principles of the present invention. The container includes a gel layer secured to a substrate which is not shown in FIG. 1;

FIG. 2 is an exploded perspective illustration of the container of FIG. 1 illustrating the top and bottom portions and a gel layer formed on a substrate;

FIG. 3 is a plan view of the bottom portion of the electrophoretic gel container according to the principles of the present invention;

DETAILED DESCRIPTION OF THE PREFERRED EMBODIMENT

Figure 4:
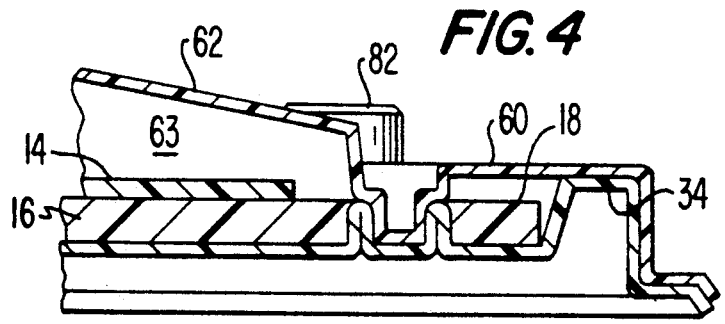
FIG. 4 is a sectional view of the electrophoretic gel container as seen in the direction of arrows 4—4 of FIG. 1.

Referring to FIGS. 1 and 2 of the drawings, a container 10 of the present invention is provided for storing and protecting an electrophoresis plate 12. The electrophoresis plate, as is conventional, includes a gel layer 14, which may be agarose gel or any other electrophoretic medium, adhered to a support substrate or backing sheet 16. The substrate 16 may preferably be a polyester film sold by E.I. du Pont under the trademark MYLAR or may be a polycarbonate film sold by General Electric under the trademark LEXAN. The substrate 16 is illustrated as being generally rectangular in configuration and having a generally flat surface upon which the gel layer is adhered. The gel layer does not extend to the edges of the flat surface of the substrate 16 and thus the peripheral surface or flat periphery 18 of the substrate 16 is free of the gel layer. A pair of spaced-apart alignment apertures 20 are provided through the substrate and these alignment apertures are located within the periphery 18 of the substrate.

The container 10 includes a top portion 26 and a bottom portion 28 which are to be secured together to enclose and protect the electrophoresis plate 12. The top and bottom portions are each preferably made of molded styrene. The top and bottom portions may be formed as a unitary part, with a hinge therebetween, or as discrete parts.

Referring primarily to FIGS. 2 and 3, the bottom portion 28 of the electrophoretic gel container will now be described. The container bottom 28 is formed as a generally flat rectangular plate having a base 30 within which base are formed a plurality of shallow, v-shaped (in plan view) stiffening corrugations. These corrugations are of shallow depth and the thickness of the corrugations in the plane of the base 30 is greater than the depth of the corrugations. Around the perimeter of the base 30 is an upwardly extending rim 34. A cavity or recess 36 is defined by the base 30 and the upwardly extending peripheral rim 34.

The bottom portion 28 is generally rectangular in configuration and is configured to receive the electrophoresis plate 12. Thus if the electrophoresis plate is square the container 10 would preferably be square. The description of the container 10 and electrophoresis plate 12, both as being generally rectangular, is solely for the purpose of illustrating the present invention. For the purposes of the present description, the container 10 may be thought of as having a front, a rear or back, and two opposed sides, the front being the portion of the container illustrated at the bottom of FIG. 3. The rim 34, at the front of the container, includes two laterally outwardly extending spaced apart projections 38, 40 and the rim at the rear of the container, includes two laterally outwardly extending, spaced apart projections 42, 44. At the front of the container 10 the rim 34 includes a recess 46 which is both downwardly curved toward base 30 and forwardly outwardly curved as illustrated in FIGS. 2 and 3. This recess 46 communicates with a rearwardly extending recess 48 in the base 30 of the container bottom. These two recesses 46, 48 facilitate removal of the electrophoresis plate 12 from the container by providing access for the thumb of a person utilizing the container of the present invention.

A lip 50 extends laterally outwardly from the rim around the periphery of the bottom portion 28, and the lip may be generally in the same plane as the base 30 of the container bottom. The lip generally follows the peripheral contour of the base 30, as seen in the plan view of FIG. 3, and includes a forwardly extending curved portion 52 at the center of the front of the container bottom, corresponding generally to the location of the rim recess 46. The lip 50 further includes an enlarged portion 54, which extends laterally outwardly, at a forward corner of the container bottom. This enlarged lip portion 54 is provided to facilitate handling of the container and to primarily facilitate opening pr separating the container top and bottom.

Figure 8:
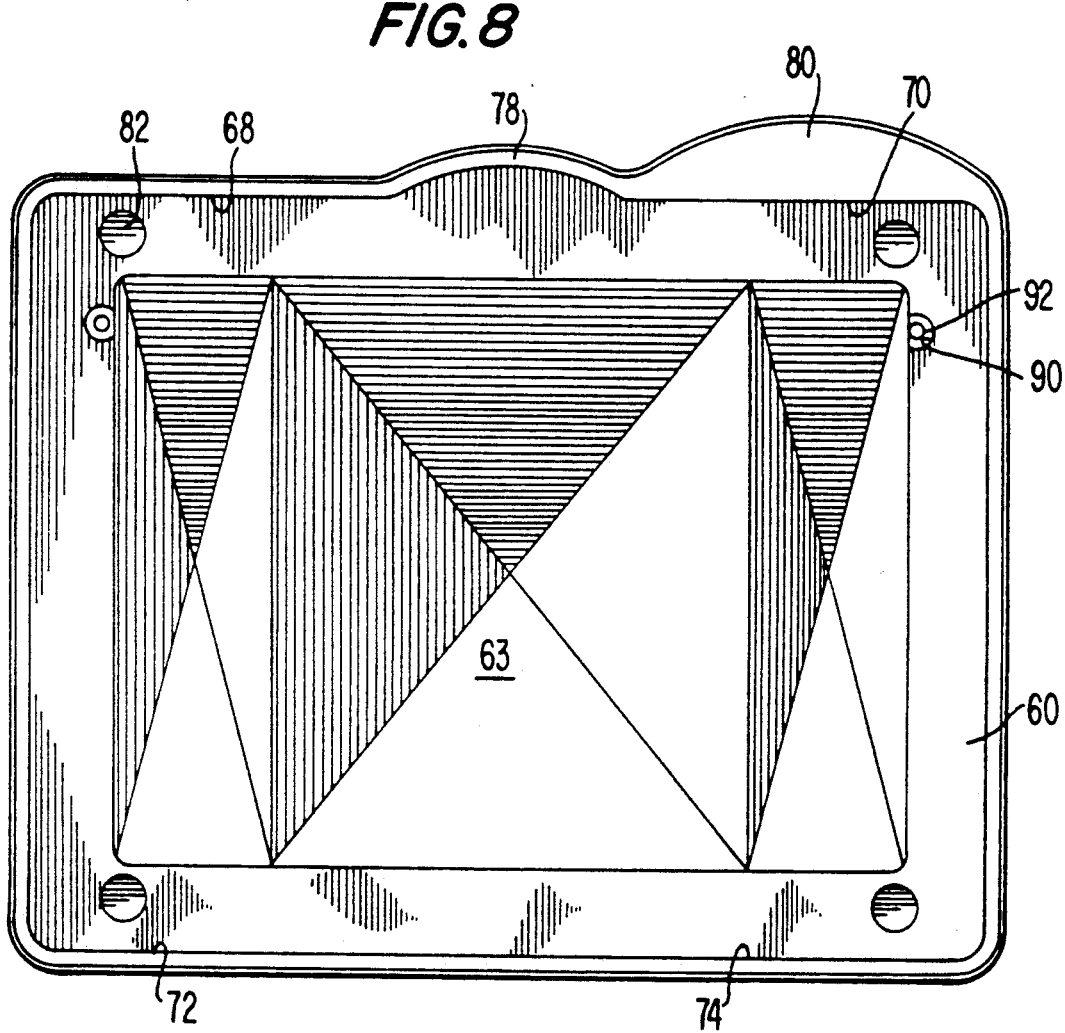
FIG. 8 is a plan view of the top portion of the electrophoretic gel container as seen from the interior of the container.

Referring next primarily to FIGS. 1, 2, and 8 the top portion 26 of the container of the present invention will now be explained. The top portion 26 is also illustrated as being of generally rectangular configuration and includes a generally rectangular base 60 having a generally rectangular, upwardly extending central portion 62. This central portion 62 may be slightly corrugated for reinforcement purposes. The central portion 62 extends upwardly from the base 60 and thus when seen in &he inverted view of FIG. 8 appears to define a downward recess 63 relative to the plane of the base 60. Recess 63 is generally aligned above cavity 36. The base 60 terminates in an outwardly extending peripheral lip 64 and a peripheral shoulder or vertical wall 66 is defined between the base 60 and the lip 64. Thus when viewed in the direction of FIG. 2, the central portion 62 is above the plane of the base 60 and the base 60 terminates in a downward vertical wall 66 and thereafter in an outwardly extending lip 64 which is below the plane of the base 60.

At the front of the base 60 two laterally spaced apart outwardly extending projections 68, 70 are provided and at the rear of the base 60 two laterally spaced apart, outwardly extending projections 72, 74 are provided. The projections 68, 70, 72 and 74 are configured to be aligned with the projections 38, 40, 42 and 44 on the bottom 28 of the container. When viewed from the interior of the top portion 26, the projections 68, 70, 72 and 74 appear as undercut portions 68', 70', 72' and 74' respectively. Thus when the top and bottom portions are force-fit together, the projections 38, 40, 42 and 44 on the bottom of the container will be force fit into and snugly received by the undercut portions 68', 70', 72' and 74' respectively. Stated alternatively, the bottom projections are sealingly engaged within the projections in the top portion 26. In fact the entire rim 34 fits snugly and sealingly within the top portion 26. This provides for a sealing relationship between the top and the bottom thus preventing or at least reducing dehydration of the gel layer 14.

The base 60 of the container top 26 includes a forwardly projecting curved portion 76 aligned above the curved portion of the lip 52 in the container bottom 28, and the lip 64 which follows the peripheral contour of the container top includes a forwardly extending, curved portion 78. One corner of the lip, illustrated as the lower right hand corner in FIG. 1 includes a lip enlargement 80. Lip enlargement 80 is illustrated as being at the front of the container but adjacent the opposite side thereof from the lip enlargement 54 on the bottom 28 of the container. The container may easily be separated by pulling lip enlargements 54 and 80 in opposite directions away from the plane of the electrophoresis plate.

According to the principles of the present invention, means are provided for supporting a plurality of aligned containers without damage to the containers and without damage to the electrophoresis plate within the container. The supporting means includes not only the corrugations 32 in the base of the container and the corrugations in the top of the container but, in addition, the base 60 at the top of the container is provided with a plurality of vertically upwardly extending stacking posts each being illustrated as circular in plan view and cylindrical in elevation view. As seen in greater detail in the sectional views of FIGS. 4 through 7, the top of each stacking post does not necessarily extend above the height of the central portion 62 of the container top. Thus the central portion of the container top initially will receive, transfer and distribute some of the weight of any containers placed thereon and, thereafter, the stacking posts will support and distribute the weight and will maintain the weight outwardly of the location of the electrophoresis plate. To reinforce the container and to reduce the potential for gel layer damage, the stacking posts 82 are laterally outwardly of the central portion 62 and of the gel layer 14 as seen in plan view.

Means are provided, according to the principles of the present invention, for securing each electrophoresis plate within its respective container. As indicated previously, each electrophoresis plate 12, and particularly the substrate 16 of each electrophoresis plate, will be provided with a plurality of spaced apart apertures 20. Prior to the present invention, the base of the containers had been provided with generally upwardly extending alignment pins which would extend through the apertures 20 in the substrate 16. However, such alignment pins did not protect the gel layer in the event that the container was rotated into a vertical position or inverted, and did not secure the container portions together.

The present invention provides a novel means for securing the electrophoresis plate in position interiorly of the container and for securing the container portions together. The securing means includes a pair of spaced apart sockets 84. Sockets 84 are preferably formed in the bottom portion 28 of the container 10 and extend upwardly from the base 30. Each socket 84, as initially formed, is of circular cross section as seen in plan view and cylindrical in elevation view, and includes an upwardly extending wall 86 and a generally flat top 88.

Figure 5:
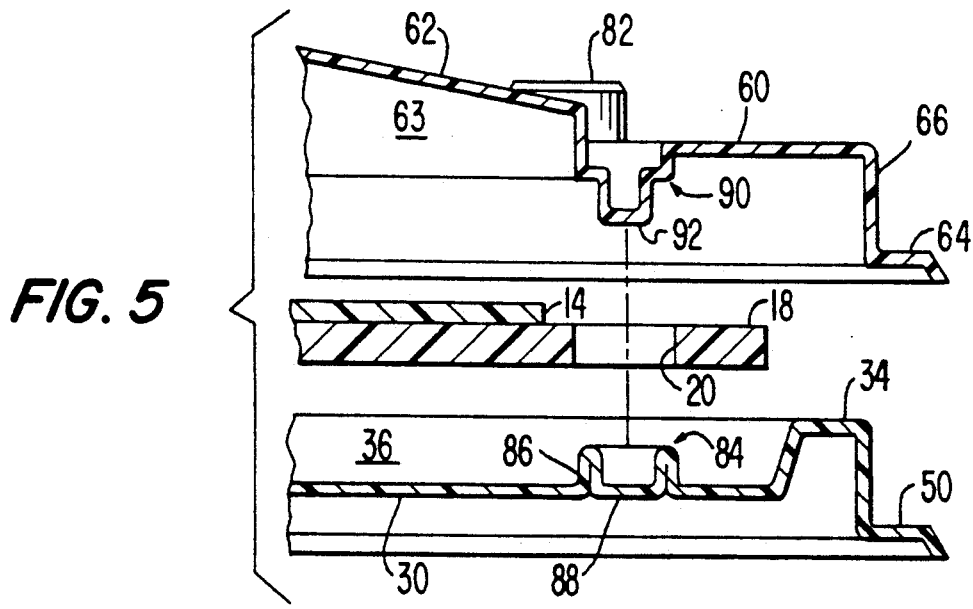
FIG. 5 is an exploded sectional view of FIG. 4.
Figure 6:
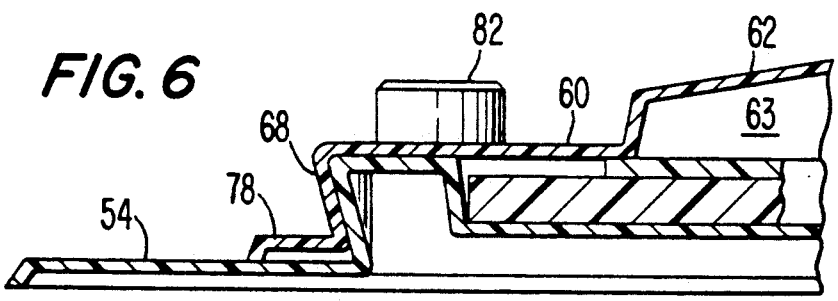
FIG. 6 is a sectional view of the container as seen in the direction of arrows 6—6 of FIG. 1.
Figure 7:
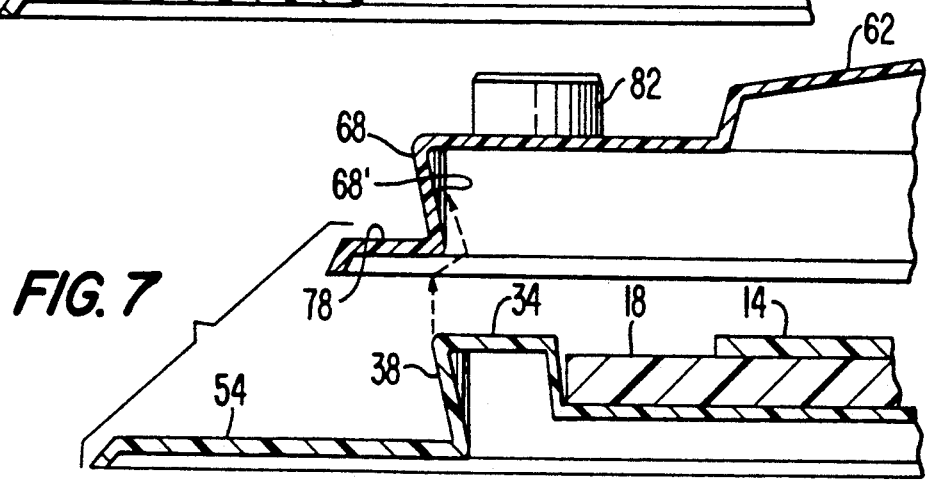
FIG. 7 is an exploded view of FIG. 6.

The securing means of the present invention further includes a plurality of locking pins 90 formed in the base 60 of the top 26, just outwardly of the central portion 62, each positioned to be aligned above a socket 84. The locking pins extend downwardly from the interior surface of the top as best illustrated in FIGS. 2, 4 and 5, and each locking pin includes a downwardly projecting tip 92.

The operation or use of the container of the present invention will now be explained. After the electrophoretic gel is adhered to the substrate 16, the substrate is placed within the bottom portion 28 of the container 10 such that the sockets 84 extend upwardly through the apertures 20 in the substrate. Thereafter, the top portion 26 is placed over the bottom 28 and forced toward the bottom. The front projections 38, 40 on the bottom of the container engage interiorly of the front projections 68, 70, (i.e., in the undercuts 68', 70') on the top of the container. The rear projections 42, 44, on the bottom of the container engage interiorly of the rear projections 72, 74 (i.e., in the undercuts 72', 74') on the top of the container. The remainder of the rim 34 on the bottom of the container fits snugly within the top of the container. This provides a substantially air-tight container to protect the electrophoresis gel against dehydration. As the top and bottom of the container are forced together, the tips 92 of the locking pins 90 deform the tops 88 of the respective sockets thus causing the top 88 of each socket to assume generally the configuration illustrated in FIG. 5. Since there is a force fit between a locking pin 90 and the wall 86 of the socket 84, even if the socket top 88 is punctured by the locking pin tip, an air-tight environment is maintained within the interior of the container. The securing means of the present invention protects the electrophoresis plate 12 even if the container is inverted. Thus if the container is inverted, the substrate 16 does not move free of the socket-locking pin combination.

As may be appreciated primarily from a review of the cross sectional figures, the periphery 18 of the substrate 16 will be positioned within the cavity 36 of the container bottom 28 and will be positioned underneath the base portion 60 of the top 26 but will not be physically contacted by the base 60. The gel 14, which is of smaller size than the substrate 16, fits generally within the dimensions of the central recess 63 of the container top 26.

The foregoing is a complete description of the preferred embodiment of the present invention. Many changes may be made without departing from the spirit and scope of the present invention. The present invention, therefore, should be limited only by the following claims.

What is claimed is:

1. A container having top and bottom portions for protecting and enclosing an electrophoresis plate, the container comprising:

one of said top and bottom portions configured as a generally flat rectangular base having an upwardly extending peripheral rim, said rim having a plurality of laterally outwardly extending projections; and the other of said top and bottom portions being configured as a generally rectangular base and having a plurality of generally laterally outwardly extending projections having complementary undercuts;

the projections on said one container portion being positioned and configured for sealingly engaging the complementary undercuts on said other container portion.

2. The invention as defined in claim 1 wherein said top and bottom portions are formed as two discrete components.

3. The invention as defined in claim 1 wherein said top portion and said bottom portion each include means to facilitate separating the top portion and bottom portion.

4. The invention of claim 1 wherein at least one of said top and bottom portions includes a central portion raised relative to the generally rectangular base, said raised central portion defining an interior recess.

5. The invention of claim 1 wherein at least one of said top and bottom portions includes weight supporting and distributing means.

6. The invention of claim 5 wherein said weight supporting and distributing means includes a plurality of upwardly extending support posts.

7. The invention of claim 1 wherein at least one of said top and bottom portions has a cavity for receiving an electrophoresis plate.

8. The invention of claim 1 wherein at least one of said top and bottom portions includes
   means for securing the top portion and bottom portion together and for preventing movement of an electrophoresis plate received between said top and bottom portions.

9. The invention of claim 8 wherein the securing means extends through the electrophoresis plate.

10. The invention as defined in claim 8 wherein the securing means includes at least one socket and at least one pin to engage the socket.

11. The invention as defined in claim 8 wherein the securing means includes at least one socket for extending through the electrophoresis plate, said socket having a deformable portion, said securing means further including a pin for engaging said socket and deforming the top of the socket.

12. The invention as defined in claim 1 wherein the container further includes reinforcing projections for receiving and distributing weight placed on the container.

* * * * *